(12) United States Patent
Schuetzle et al.

(10) Patent No.: US 11,994,345 B2
(45) Date of Patent: *May 28, 2024

(54) PROCESS FOR THE COMMERCIAL PRODUCTION OF HIGH-QUALITY CATALYST MATERIAL

(71) Applicant: GREYROCK TECHNOLOGY, LLC, Sacramento, CA (US)

(72) Inventors: Robert Schuetzle, Sacramento, CA (US); Dennis Schuetzle, Grass Valley, CA (US)

(73) Assignee: Greyrock Technology, LLC, Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/803,671

(22) Filed: Oct. 4, 2022

(65) Prior Publication Data

US 2023/0213284 A1 Jul. 6, 2023

Related U.S. Application Data

(63) Continuation of application No. 16/602,770, filed on Dec. 4, 2019, now Pat. No. 11,493,274.

(51) Int. Cl.
*F27D 3/00* (2006.01)
*B01J 23/755* (2006.01)
(Continued)

(52) U.S. Cl.
CPC .......... *F27D 3/0033* (2013.01); *B01J 23/755* (2013.01); *B01J 35/31* (2024.01); *B01J 35/63* (2024.01);
(Continued)

(58) Field of Classification Search
CPC .......... B01J 23/755; B01J 35/00256; B01J 35/1033; B01J 35/1052; B01J 35/108;
(Continued)

(56) References Cited

U.S. PATENT DOCUMENTS 4,150,246 A * 4/1979 Taylor ............... B01J 23/36
502/185
7,449,425 B2 * 11/2008 Wang ............... B01J 23/78
502/328

(Continued)

*Primary Examiner* — Patricia L. Hailey
(74) *Attorney, Agent, or Firm* — Jeffrey A. McKinney; McKinney Law Group APC

(57) ABSTRACT

The present invention describes an improved process for the commercial scale production of high-quality catalyst materials. These improved processes allow for production of catalysts that have very consistent batch to batch property and performance variations. In addition these improved processes allow for minimal production losses (by dramatically reducing the production of fines or small materials as part of the production process). The improved process involves multiple steps and uses calcining ovens that allow for precisely control temperature increases where the catalyst is homogenously heated. The calcining gas is released into a separate heating chamber, which contains the recirculation fan and the heat source. Catalysts that may be produced using this improved process include but are not limited to catalysts that promote CO hydrogenation, reforming catalysts, Fischer Tropsch Catalysts, Greyrock Grey-Cat™ catalysts, catalysts that homologate methanol, catalysts that promote hydrogenation of carbon compounds, and other catalysts used in industry.

15 Claims, 1 Drawing Sheet

(51) Int. Cl.
*B01J 35/31* (2024.01)
*B01J 35/63* (2024.01)
*B01J 35/64* (2024.01)
*B01J 35/66* (2024.01)
*B01J 37/08* (2006.01)
*F27D 3/16* (2006.01)
*F27D 5/00* (2006.01)
*F27D 9/00* (2006.01)
*F27D 19/00* (2006.01)

(52) U.S. Cl.
CPC ............... *B01J 35/64* (2024.01); *B01J 35/66* (2024.01); *B01J 37/08* (2013.01); *F27D 5/0068* (2013.01); *F27D 2003/0034* (2013.01); *F27D 2003/166* (2013.01); *F27D 2009/0002* (2013.01); *F27D 2019/0056* (2013.01); *F27D 2019/0093* (2013.01)

(58) Field of Classification Search
CPC .... B01J 37/08; B01J 8/0285; B01J 2208/024; B01J 2208/065; B01J 2208/00044; B01J 2208/00017; B01J 2208/00884; B01J 23/02; B01J 23/06; B01J 23/28; B01J 23/40; B01J 23/72; B01J 23/74; F27D 3/0033; F27D 5/0068; F27D 2003/0034; F27D 2003/166; F27D 2009/0002; F27D 2019/0056; F27D 2019/0093
USPC .... 502/5, 523, 305, 307, 315, 316, 318, 326
See application file for complete search history.

(56) References Cited

U.S. PATENT DOCUMENTS

| | | | |
|---|---|---|---|
| 11,493,274 B2 * | 11/2022 | Schuetzle | ................ B01J 37/08 |
| 2015/0031922 A1 * | 1/2015 | Schuetzle | ............... C22C 19/07 |
| | | | 502/328 |
| 2021/0340075 A1 * | 11/2021 | Schuetzle | ............... B01J 23/892 |

* cited by examiner

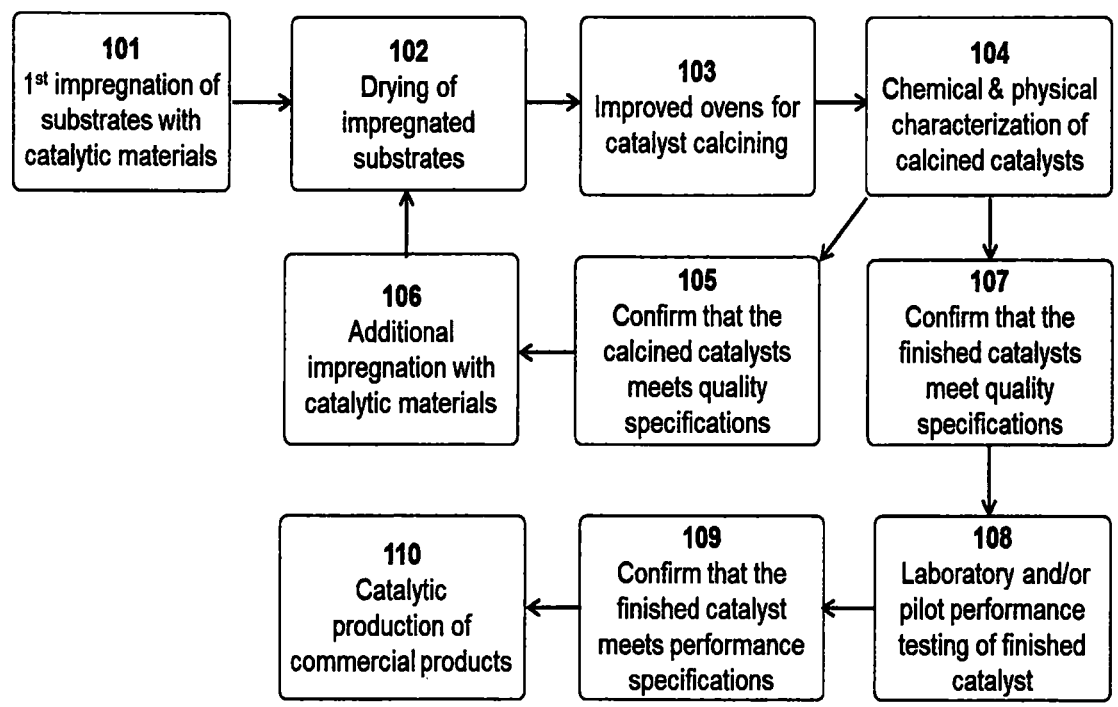

PROCESS FOR THE COMMERCIAL PRODUCTION OF HIGH-QUALITY CATALYST MATERIAL

This application is a continuation of U.S. patent application Ser. No. 16/602,770, filed on Dec. 4, 2019, which is incorporated by reference for all purposes.

FIELD OF THE INVENTION

The present invention describes an improved process for the production of high-quality catalyst materials. Shapes of such catalyst materials may include spheres, pellets, cylinders, cones, stars, pyramids, trilobes and quadralobes and other shapes that are commonly used in the art. This innovation is made possible by homogeneous heating of the catalyst materials throughout an oven at accurate temperature programming rates and controlled air or gas flow throughout the oven. As a result of these advancements, finished catalysts have batch to batch property and performance variations of less than about 50%, preferably less than 25%, more preferably less than 10%, and even more preferably less than 5%. Catalyst production losses, as a result of not meeting quality specifications, are less than about 50%, preferably less than 25%, more preferably less than about 10% and even more preferably less than 5%.

BACKGROUND OF THE INVENTION

Many types of catalyst materials have been developed for the conversion of syngas, olefins, carbon dioxide and other reactants to fuels and chemicals (Regalbuto, 2006; Fisher et. al, 2016; Munnik et. al, 2015). These catalyst materials have been developed to accommodate the large differences in operating conditions, feedstocks, and desired products, and the catalytically active metals can be deposited on a range of supports/substrates, which are generally highly porous and can vary in size from small powders to centimeter-sized pellets or larger. In each case, high activities and selectivities toward the desired products are required.

Catalyst particles can vary widely in terms of chemical composition and physical characteristics. These catalyst particles are typically referred to as catalyst substrates. Some common substrates include alumina, silica, carbon and combinations thereof. These substrates often contain various levels of impurities. The catalyst substrate may be formed in the shape of spheres, pellets, cylinders, cones, stars, pyramids, trilobes and quadralobes and other shapes that are commonly used in the art. Catalyst particles have many advantages, such as high surface area, high mechanical strength and excellent thermal stability.

Catalyst formulations are comprised of one or more inorganic compounds that are blended together at specified concentrations. These inorganic compounds are typically nitrates, sulfates, acetates, chloride or carbonates of various metals (e.g. metal salts). These compounds are dissolved in water and/or solvents so that they can be impregnated into the substrate.

A typical manufacturing process for catalyst materials may include: 1. Preparation of the catalyst formulation in water and/or solvents; 2. Impregnation (coating) of the catalytic formulation on the substrate; 3. Removal of water and/or solvents from the substrate; and 4. Calcination in which the catalytic material is heated at different temperatures and rates. These steps may be repeated one or more times and steps may be varied depending upon the specific catalyst (De Jong, 2009)

The impregnation process (1) may be carried out by adding a specific quantity of the dissolved catalyst solution to the catalyst particles (2). The catalyst solution added in excess of the support pore volume causes the solution to diffuse into the catalyst particles. The catalyst particles are then dried (3) and calcined (4) to convert the metal salts into metal oxides.

Gas-phase constituents are evolved during the calcining process and the types of gases emitted is dependent upon the composition of the metal salts as follows:

a. Nitrates produce NO and $NO_2$
b. Sulfates produce $SO_2$ and $SO_3$
c. Acetates produce $C_2H_4O_2$ (acetic acid)
d. Chlorides produce HCl and $Cl_2$
e. Carbonates produce $CO_2$ These gas-phase materials need to be removed at a specified rate in order for the catalyst calcining to be effective.

Although the development and preparation of catalysts have been investigated for many years, numerous aspects of the various catalyst manufacturing steps are still not fully understood, and the design and scale-up of commercial catalyst manufacturing processes are often done by trial and error.

In addition to the substrate properties and catalyst formulation, the performance of a commercial catalyst is very dependent upon the processes used to manufacture the catalyst.

The performance of the manufactured catalyst is determined by measuring its chemical and physical properties and assessing its performance using laboratory and/or pilot scale catalytic reactors.

Key chemical property specifications for the finished catalyst include but are not limited to: 1. Elemental composition; 2. Molecular structure and 3. Contaminant concentrations. Important physical property specifications for the finished catalyst include: 1. Shape, size and aspect ratios of the catalyst particles; 2. Crush strength and hardness; 3. Pore diameter; 4. Pore volume; 5. Surface area; 6. Catalyst crystallinity, crystallite size and crystallite coverage (Khodakov et al, 2007).

The catalytic reactors that are typically used for performance testing include single-tube, multi-tubular, slurry, trickle bed, moving bed, fluidized bed, or micro-channel systems. Catalyst performance testing is carried out by using various mixtures of gases ($H_2$, CO, $CH_4$, $CO_2$, hydrocarbons, etc.) under different catalyst operating conditions (temperature, pressure and space velocity).

Typical catalyst performance specifications include: 1. Catalyst productivity (e.g. how much product is produced from a quantified amount of catalyst under defined catalyst operating conditions); 2. High selectivity for the preferred products; 3. Low selectivity for the side products; 4. Long term (>1,000 hrs.) catalyst durability tests; and other tests typically carried out to assess catalyst performance.

The proper design and optimization of catalyst manufacturing processes can significantly reduce batch-to-batch variability and production costs. Catalysts manufactured with a high level of quality reduce feedstock requirements and energy use through improved reaction yields and product selectivity's.

Since catalyst calcining was considered to be an art rather than a science for several decades, the International Union of Pure and Applied Chemistry (IUPAC) was asked in 1995 to develop and published recommendations for catalyst calcination. They recommended that catalyst batches should be subjected to identical calcining conditions and that special consideration needs to be given to mass and heat transfer in the calcining ovens in order to manufacture high-quality catalysts (Haber et. al, 1995).

Since the IUPAC recommendations, several laboratory studies have been reported on the effect of heating rate, gas composition, gas space velocity and other factors on the calcining of catalysts using different types of calcining ovens and furnaces.

Van de Loosdrecht et al (2003) described the preparation of several Fischer-Tropsch type catalysts and compared different laboratory calcining processes and conditions on the chemical/physical properties and performance of the catalysts. Catalyst calcining was carried out using a laboratory rotary kiln furnace and a stationary oven. They determined that catalyst calcining using rotary kiln furnaces or stationary calcinations can be performed successfully if the catalyst layer thickness is kept small (less than about 1.0 cm) and if the heating rate can be controlled accurately. However, they concluded that these are not commercially attractive options and therefore no recommendations on how to design and build commercial scale calcining ovens were proposed.

Jentoft et al (2003) reviewed the current art for the thermal treatment of catalysts and found that existing calcining ovens experienced many shortcomings as follows:

a. The temperature controllers and programmers were not accurate.
b. There was high temperature variability in different areas of the oven which resulted in non-uniform heating of the catalysts.
c. There was a temperature lag of oven temperature behind the programmed temperature which in some cases was due to insufficient power to the oven;
d. The catalyst temperature was different than that of the oven temperature.

In 2018, Vedrine reviewed the established art on different calcining processes for the production of finished catalysts. It was found that fluidized bed calcination resulted in a significant attrition loss of catalyst material. Detailed studies were carried out to determine batch to batch variation in the chemical and physical properties for a Molybdenum type catalyst prepared by calcining in a stationary oven. X-ray diffraction analysis was carried out to determine the variability in $MoO_6$ concentration in Molybdenum mixed oxide catalysts. Fifteen percent batch to batch variations of $MoO_6$ in the catalyst were observed.

Despite the many types of catalysts that have been developed, there is still a need in the art for novel processes to improve catalyst quality and reduce the loss of catalysts that don't meet performance specifications.

BRIEF SUMMARY OF THE INVENTION

In one aspect, the present invention provides a catalyst production process that includes a calcining step where heating and gas flow rates are precisely controlled, resulting in the production of high-quality catalysts that meet batch-to-batch chemical, physical and performance specifications with a high level of reproducibility. The calcining process includes the steps of: heating the calcining gas in one or more separate chambers, each of which contains a recirculation fan and thermostatically controlled heat source; circulating the calcining gas around a dried catalyst in a fixed bed, wherein the dried catalyst is evenly filled in one or more oven trays or on a belt (in the case of a moving bed) to a depth ranging from 1 cm to 100 cm, preferably 10 cm, and wherein the amount of catalyst in the oven is greater than about 10 kg, but preferably greater than 100 kg; recirculating the calcining gas around the dried catalyst at least about 3 times, but preferably greater than 10 times; increasing the oven temperature to a desired temperature in increments ranging from about 0.1° F./min to about 50° F./min. but preferably 0.5° F./min, with an average accuracy better than about 50%, 25%, 10% or 5%, such that the temperature at any area within the oven does not vary by more than 50%, 25%, 15%, 10% or 5%; maintaining the oven at the desired temperature for a predetermined amount of time; cooling the oven to ambient temperature at a controlled rate ranging from about 2° F./min. to about 20° F./min, thereby producing a calcined catalyst that has batch to batch property and performance variations of less than about 50%, preferably less than 25%, more preferably less than about 15% and more preferably less than about 5%.

BRIEF DESCRIPTION OF THE DRAWINGS

FIG. 1 illustrates the improved catalyst manufacturing process including a calcining process step for the production of high-quality structured catalysts.

DETAILED DESCRIPTION OF THE INVENTION

Structured catalysts are traditionally calcined commercially using rotary, fluidized-bed and moving bed furnaces. These are aggressive manufacturing processes which typically cause breakage and abrasion of catalysts. In addition, catalyst calcination temperatures, heating rates and air flows are difficult to control. As a result, it has been discovered that finished catalysts have considerable batch to batch variations in performance.

This invention describes processes that can be used at commercial scale and have been designed to overcome these problems. These improved processes precisely control temperature increases, the temperature variations within the calcining oven enclosure is small, and the catalyst is homogenously heated. The calcining gas (typically air, but also including options for nitrogen, $CO_2$ or other gases) is released into a separate heated chamber, which contains the recirculation fan and the heat source which uses gas-fired burners or electric heaters. A tunnel is used to connect the directly heated chamber to calcining oven enclosure. The process control system is used to adjust the air or gas flow through the tunnel to program specific temperature increases or decreases and to maintain homogenous temperatures in the calcining oven chambers.

It has been established that the amount of recirculated air or other gases should be relatively high, in order to successfully transfer heat homogenously to the catalyst. The prepared catalysts are loaded onto trays manually or mechanically and the trays are introduced into the ovens.

Trays that hold the catalyst material in the oven may be solid trays or alternative designs such as mesh trays. Trays may take a variety of shapes including rectangular, square, circular, trapezoidal, or other shapes. Materials of construction of the trays may include metals, ceramics or other materials that can function at the temperatures and operating conditions of the calcining oven.

The following description is of a general process of the present invention in relation to FIG. 1. The catalysts are prepared by impregnation of the catalytic materials on the substrates 101 and the impregnated substrates are dried 102. The dried catalysts are calcined in the improved calcining ovens 103 and chemical and physical characterization 104 is carried out to determine if the calcined catalysts meet quality specifications 105. If the calcined catalysts meet quality specifications then additional impregnation of the catalytic materials on the calcined catalysts is carried out (if required) 106, dried 102 and calcined in the improved calcining ovens 103. Chemical and physical characterization 104 is carried out to determine if the calcined catalysts meet quality specifications 105. If this is the final calcination and the calcined catalyst meets quality specifications 107, then laboratory and/or pilot testing is carried out 108 to verify that the finished catalysts meet performance specifications 109. If the finished catalysts meet performance specifications 109 then the catalysts can be used for production of commercial products 110.

In one case, the present invention provides a catalyst calcining process where heating and gas flow rates are precisely controlled, resulting in the production of high-quality catalysts that meet batch-to-batch chemical, physical and performance specifications with a high level of reproducibility. In one embodiment, the heating gas is heated in a separate reheating chamber and is transferred to the calcining oven via a passageway. The process may be performed in a calcining oven that has fixed (stationary) beds, although suitable moving beds may be used in certain circumstances. Moving beds may include beds that use belts or moving trays to move the catalyst through the heating zone. The oven is typically capable of heating calcining gas in one or more separate chambers, each of which contains a recirculation fan and thermostatically controlled heat source. The calcining gas is circulated, and recirculated (usually at least about 3 times, 10 times, or about 15 times or about 20 times or about 25 times or about 50 times), in one or more areas of the calcining oven that include a dried catalyst, which is evenly filled in one or more oven trays to a depth of from about 0.5 cm to about 100 cm (or about 1 cm to about 10 cm, or about 1 cm to about 9 cm, or about 1.25 cm to about 8 cm, or about 1.5 cm to about 7 cm, or about 1.75 cm to about 6 cm, or about 2 cm to about 5 cm, to about 10 cm, to about 20 cm in certain cases).

The catalyst to be calcined is typically prepared by impregnating a substrate with one or more inorganic salts that have been dissolved in an aqueous solution or one or more organic solvents. Oftentimes the aqueous solution or organic solvent(s) are removed from the impregnated catalyst using a drying oven at a temperature lower than about 600° F. (or about 500° F., or about 450° F., 375° F., or about 350° F., or about 325° F., or about 300° F., in certain cases) to provide a dried catalyst.

The stationary or moving bed calcining oven is capable of being programmed from ambient temperature to about 2,000° F. The programmed oven temperature can be increased over the desired temperature range from about 0.5° F. to about 10° F. (or about 0.5° F. to about 6.5° F., or about 1.0° F. to about 3.0° F., in certain cases), typically with an average accuracy better than about 50% (or about 25%, or about 15%, or about 10%, or about 9%, or about 8%, or about 7%, or about 6%, or about 5%, in certain cases). The desired temperature at any area within the oven typically does not vary by more than about 50% (or about 25%, or about 15%, or about 10%, or about 5%, or about 4%, or about 3%, in certain cases). The catalyst can usually be cooled from about 2,000° F. down to ambient temperature at a controlled rate ranging from about 2° F./min. to about 20° F./min. (or about 2° F./min. to about 17.5° F./min., or about 2° F./min. to about 15.0° F./min., or about 2° F./min. to about 12.5° F./min., or about 2° F./min. to about 10.0° F./min., in certain cases).

Non limiting examples of catalysts that can be produced by the process of the present invention include:

Catalysts that Promote CO Hydrogenation—These catalysts produce hydrocarbons and oxygenated hydrocarbons from mixtures of carbon monoxide and hydrogen. A wide range of products can be produced depending upon the chemical and physical properties of the catalyst utilized and the conditions under which the catalyst is run (e.g., temperature, pressure, space velocity) and the presence of other gases (e.g., $O_2$, $N_2$, $CH_4$, and $CO_2$). Such products may include $CH_4$; $C_5$-$C_{23}$ liquid-phase hydrocarbons; $C_{24}$-$C_{80}$ solid-phase hydrocarbons (e.g. waxes); alcohols; aldehydes; and acids. Some examples of these catalysts are summarized below.

Fischer-Tropsch (F-T) Catalysts—F-T catalysts primarily produce waxes with selectivity's greater than about 60% (Zhou et al, 2019). These catalysts are typically comprised of cobalt and/or iron impregnated on various substrates. Promoters such as precious metals and alkali metals are sometimes added to increase catalyst productivity or improve stability. The iron F-T catalysts produce minor concentrations of napthenes and aromatics whereas the cobalt F-T catalyst produce none of these compounds.

Gaderzi et al. (2012) found that variations in catalyst calcining conditions have a significant effect on the composition and performance of cobalt/silica F-T catalysts. These effects included:

a. The relative concentrations of $Co^{+3}$ and $Co^{+2}$ oxides in the bulk catalyst;
b. A variation in the concentration of surface Co by up to eleven times.
c. Changes in catalyst productivity by up to two times and;
d. Changes in the distribution of hydrocarbon products (e.g. from lighter to heavier).

Greyrock Greycat Catalysts—Greycat catalysts were developed to produce $C_5$-$C_{23}$ liquid hydrocarbons (Schuetzle et al., 2013) with a high selectivity of greater than about 50%, or greater than about 60%, or greater than 70% or greater than 85%. The catalyst shape is ideally an extrudate with lobed, fluted, or vaned cross sections but could also be a sphere, granule, powder, or other support shape that allows for efficient operation. The use of a lobed structure, for example, enables a significant increase in the ratio of area to volume in the catalytic reactor, thus improving the volumetric efficiency of a catalytic reactor system. The lobed structures also provide an improved pressure drop, which translates into a lower difference in the pressure upstream and downstream of the catalyst bed, especially when they are used in fixed bed reactors. The effective pellet radius of a pellet or support refers to the maximum radius which is a distance from the mid-point of the support to the surface of the support. For lobed supports, the effective pellet radius refers to the minimum distance between the mid-point and the outer surface portion of the pellet. In embodiments of the invention, the effective pellet radius may be about 600 microns or less. In one embodiment, the effective pellet radius may be about 300 microns or less. In embodiments of the invention, the pellet or support material may be porous. The mean pore diameter of the support material may be greater than 50 angstroms. In one embodiment, the pellet or support material may have a mean pore diameter greater than about 100 angstroms. In one embodiment, the pellet or support material may have a mean pore diameter greater than about 120 angstroms Any suitable material can be used as a support material in the catalytic process. These include metal oxides, such as alumina, silica, zirconia, magnesium, or combinations of these materials. Preferably, silica or alumina or combinations of these materials including structural promoters are used as a support material to make a supported catalyst. The catalytically active metals, which are included with or dispersed to the support material, include substances which promote the production of diesel fuel in the catalytic reaction. For example, these metals may include cobalt, iron, nickel, or any combinations thereof. Various promoters may be also added to the support material. Examples of promoters include palladium, platinum, gold, nickel, rhenium, iridium, ruthenium, silver, osmium or any combinations thereof. The catalyst support ideally has crush strength of between than 3 lbs/mm and 4.5 lbs/mm and a BET surface area that is greater than 150 $m^2/g$. This combination of variables is unique. Conventional high surface area supports have an average pore diameter less than 100 angstroms. Supports that have been engineered to have a large average pore volume greater than 120 angstroms will have surface area much lower than 150 $m^2/g$ and crush strength will be below 2 lbs/mm despite additional calcination or heat treatment. This combination of properties may be achieved with the addition of a structural stabilizer that provides additional crystallinity (for example silicon or silica oxide) and thus more strength upon heat treatment. The active metal distribution on the support is ideally between about 2% and about 10%, preferably about 4%. The active metal dispersion is the fraction of the atoms on the catalyst surface that are exposed as expressed by: $D=N_S/N_T$, where D is the dispersion, $N_S$ is the number of surface atoms, and $N_T$ is the total number of atoms of the material. Dispersion increases with decreasing crystallite size. In one embodiment, a supported catalyst includes cobalt, iron, or nickel deposited at between about 5 weight % and 30 weight % on gamma alumina, more typically about 20 weight % on gamma alumina, based on the total weight of the supported catalyst. Also, the supported catalyst formulation includes selected combinations of one or more promoters consisting of palladium, platinum, gold nickel, rhenium, ruthenium, iridium, and combinations in about 0.01-2.0 weight % range, more typically in about 0.1-0.5 weight % range per promoter. Production methods of the catalyst include impregnation and other methods of production commonly used in the industry and are described in the art.

Catalysts that Promote $CO_2$ Hydrogenation—These catalysts primarily produce methane, carbon monoxide or methanol, depending upon the catalyst composition and operating conditions. In certain embodiments the catalyst is composed of the constituent elements—Ni, Cu, Zn, Mg, Mo or Fe in free or combined form. Minor amounts of Ru, Rh and Pd are sometimes added as promoters. The weight percent of each constituent element in the hydrogenation catalyst component has a preferred range. The weight percent of metal to support is approximately 0.001% to 50% and preferably approximately 0.01% to 20%, depending on the specific surface area of the support. The ratio of the primary metals ranges from 0.01 to 50, preferably 0.1 to 5 by molar ratio. The ratio of any alkali metal promoter to the primary metals ranges from 0.0001 to 5, preferably 0.001 to 3 by molar ratio.

Catalysts that Homologate Methanol—These catalysts promote the homologation of methanol with hydrogen and carbon monoxide. Certain embodiments of the catalyst include a catalyst with one or more Group VIII metals (including Fe, Co, Ni, Rh, Ru, Os, Pt, Pd) in free or combined form with one or more co-catalyst metals including Yttrium (Y) or one of the lanthanide series (including La, Ce, Pr, Nd, Pm, Sm, Eu, Gd, Tb, Dy, Ho, Er, Tm, Yb, Lu) or the actinide series (including Ac, Th, Pa, U, Np, Pu, Am, Cm, Bk, Cf, Es, Fm, Md, No in free or combined form. The ratio of each constituent element in the homologation catalyst components also has a preferred range. The weight percent of Group VIII metals to support is 0.0001 to 1, preferably 0.001 to 0.5, depending on the compound and the specific surface area of the support substrate 212. The ratio of yttrium, lanthanide series, or actinide series metal to Group VIII metal is 0.001 to 50, preferably 0.005 to 20 by molar ratio. The ratio of any alkali or other metal promoter to Group VIII metal may be within the range of 0.0001 to 10, preferably 0.001 to 5 by molar ratio.

Catalysts that Promote Hydrogenation of Carbon Compounds—These catalysts are used to reduce double and triple bonds in hydrocarbons (Hudlicky, 1996). These catalysts are typically comprised of Ni, Pd or Pt.

Typically, the process of the present invention is used to calcine catalysts in quantities greater than about 10 kg per batch. In certain cases, catalysts are calcined in quantities greater than about 50 kg per batch, 100 kg per batch, 150 kg/batch, 200 kg/batch, 250 kg/batch, 300 kg/batch, 350 kg/batch, 400 kg/batch, 450 kg/batch or 500 kg/batch. In other cases, catalysts are calcined in quantities greater than about 750 kg/batch, 1,000 kg/batch, 1,250 kg/batch or 1,500 kg/batch.

Catalysts produced using the process of the present invention usually have a batch to batch property and performance variations of less than about 50 percent, 25 percent, 15 percent, 10 percent, 7.5 percent, 5 percent, 4 percent, or 3 percent. In certain cases, the batch to batch property and performance variations are less than about 2.5 percent, 2 percent or 1.5 percent.

Oftentimes, catalysts produced using the process of the present invention have a production efficiency (in some cases quantified as the percentage conversion of the carbon in the feedstock to liquid fuels) at least about 1 percent more that catalysts produced from a traditional process. The carbon containing feedstock may include CO, $CO_2$, hydrocarbons, oxygenated hydrocarbons or combinations thereof. In certain cases, the production efficiency is at least about 2.5 percent, 5.0 percent, 7.5 percent, 10.0 percent, 12.5 percent, 15.0 percent, 17.5 percent, 20.0 percent, 25.0 percent, or more than 50.0 percent.

For catalysts produced using the process of the present invention that have different aspect ratios (e.g. cylinders, tablets, trilobes, etc.), the aspect ratio of the manufactured catalyst is within about 25%, about 10%, about 7.5%, about 5.0% or about 3.0% of the original substrate.

Catalysts produced using the process of the present invention that have nearly equivalent aspect ratios (e.g. spheres, cubes, etc.), the dimensions of the manufactured catalyst is within about 10%, about 7.5%, about 5.0%, or about 3.0% of the original substrate.

Catalysts produced using the processes of the present invention typically have two or more physical and chemical properties that are within about 25% of the original substrate. In certain cases, the two or more physical and chemical properties are within about 15%, about 10%, about 5%, or about 2.5% of the original substrate.

Catalysts produced using the process of the present invention typically has average pore volume that is within about 25% of the original substrate. In certain cases, the average pore volume is within about 15%, about 10%, about 5%, or about 2.5% of the original substrate.

Catalysts produced using the process of the present invention typically have primary reactant conversion efficiencies within about 25% of the established performance quality specifications. In certain cases, the primary reactant conversion efficiency is within about 15%, about 10%, about 5% or about 2.5% of the established performance quality specifications.

Catalysts produced using the process of the present invention typically has primary product selectivities that are within about 25% of the established performance quality specifications. In certain cases, the primary product selectivity is within about 15%, about 10%, about 5% or about 2.5% of the established performance quality specifications.

Catalysts produced using the process of the present invention typically has secondary product selectivities that are within about 25% of the established performance quality specifications. In certain cases, the secondary product selectivity is within about 15%, about 10%, about 5% or about 2.5% of the established performance quality specifications.

The following are non-limiting process aspects of the present invention:

1. A catalyst calcining process where heating and gas flow rates are precisely controlled, resulting in the production of high-quality catalysts that meet batch-to-batch chemical, physical and performance specifications with a high level of reproducibility. The process is performed in a calcining oven that has either fixed (stationary) or moving beds. The oven heats calcining gas in one or more separate chambers, each of which contains a recirculation fan and thermostatically controlled heat source. The calcining gas is circulated, and recirculated at least about 10 times, in one or more areas of the calcining oven that include a dried catalyst, which is evenly filled in one or more oven trays to a depth of from about 0.5 cm to about 20 cm. The oven temperature increases during the calcining process to a desired temperature range at increments ranging from about 0.5° F. to about 10° F., with an average accuracy better than about 50%. The desired temperature at any area within the oven typically does not vary by more than 25%. After maintaining the temperature for a desired period of time, the catalyst is cooled down to ambient temperature at a controlled rate ranging from about 2° F./min. to about 20° F./min. The amount of catalyst calcined in the process is greater than about 100 kg/batch. The calcined catalyst has batch to batch property and performance variations of less than about 25 percent and an aspect ratio that is within about 25% of the original substrate.

2. A catalyst calcining process where heating and gas flow rates are precisely controlled, resulting in the production of high-quality catalysts that meet batch-to-batch chemical, physical and performance specifications with a high level of reproducibility. The process is performed in a calcining oven that has fixed (stationary) or moving beds. The oven heats calcining gas in one or more separate chambers, each of which contains a recirculation fan and thermostatically controlled heat source. The calcining gas is circulated, and recirculated at least about 10 times, in one or more areas of the calcining oven that include a dried catalyst, which is evenly filled in one or more oven trays to a depth of from about 1 cm to about 10 cm. The oven temperature increases during the calcining process to a desired temperature range at increments ranging from about 0.5° F. to about 10° F., with an average accuracy better than about 25%. The desired temperature at any area within the oven typically does not vary by more than 25%. After maintaining the temperature for a desired period of time, the catalyst is cooled down to ambient temperature at a controlled rate ranging from about 2° F./min. to about 20° F./min. The amount of catalyst calcined in the process is greater than about 100 kg/batch. The calcined catalyst has batch to batch property and performance variations of less than about 25% and an aspect ratio that is within about 25% of the original substrate.

3. A catalyst calcining process where heating and gas flow rates are precisely controlled, resulting in the production of high-quality catalysts that meet batch-to-batch chemical, physical and performance specifications with a high level of reproducibility. The process is performed in a calcining oven that has fixed (stationary) or moving beds. The oven heats calcining gas in one or more separate chambers, each of which contains a recirculation fan and thermostatically controlled heat source. The calcining gas is circulated, and recirculated at least about 5 times, in one or more areas of the calcining oven that include a dried catalyst, which is evenly filled in one or more oven trays to a depth of from about 1 cm to about 10 cm. The oven temperature increases during the calcining process to a desired temperature range at increments ranging from about 0.5° F. to about 10° F., with an average accuracy better than about 10%. The desired temperature at any area within the oven typically does not vary by more than 5%. After maintaining the temperature for a desired period of time, the catalyst is cooled down to ambient temperature at a controlled rate ranging from about 2° F./min. to about 20° F./min. The amount of catalyst calcined in the process is greater than about 100 kg/batch. The calcined catalyst has batch to batch property and performance variations of less than about 10 percent and an aspect ratio that is within about 10% of the original substrate.

4. A catalyst calcining process where heating and gas flow rates are precisely controlled, resulting in the production of high-quality catalysts that meet batch-to-batch chemical, physical and performance specifications with a high level of reproducibility. The process is performed in a calcining oven that has fixed (stationary) or moving beds. The oven heats calcining gas in one or more separate chambers, each of which contains a recirculation fan and thermostatically controlled heat source. The calcining gas is circulated, and recirculated at least about 15 times, in one or more areas of the calcining oven that include a dried catalyst, which is evenly filled in one or more oven trays to a depth of from about 1.5 cm to about 7 cm. The oven temperature increases during the calcining process to a desired temperature range at increments ranging from about 0.5° F. to about 6.5° F., with an average accuracy better than about 7%. The desired temperature at any area within the oven typically does not vary by more than 4%. After maintaining the temperature for a desired period of time, the catalyst is cooled down to ambient temperature at a controlled rate ranging from about 2° F./min. to about 15° F./min. The amount of catalyst calcined in the process is greater than about 150 kg/batch. The calcined catalyst has batch to batch property and performance variations of less than about 7.5 percent and an aspect ratio that is within about 7.5% of the original substrate.

5. A catalyst calcining process where heating and gas flow rates are precisely controlled, resulting in the production of high-quality catalysts that meet batch-to-batch chemical, physical and performance specifications with a high level of reproducibility. The process is performed in a calcining oven that has fixed (stationary) beds. The oven heats calcining gas in one or more separate chambers, each of which contains a recirculation fan and thermostatically controlled heat source. The calcining gas is circulated, and recirculated at least about 20 times, in one or more areas of the calcining oven that include a dried catalyst, which is evenly filled in one or more oven trays to a depth of from about 2.0 cm to about 5 cm. The oven temperature increases during the calcining process to a desired temperature range at increments ranging from about 1.0° F. to about 3.0° F., with an average accuracy better than about 5%. The desired temperature at any area within the oven typically does not vary by more than 3%. After maintaining the temperature for a desired period of time, the catalyst is cooled down to ambient temperature at a controlled rate ranging from about 2° F./min. to about 10° F./min. The amount of catalyst calcined in the process is greater than about 200 kg/batch. The calcined catalyst has batch to batch property and performance variations of less than about 5.0 percent and an aspect ratio that is within about 5.0% of the original substrate.

EXAMPLES

Several examples of the embodiments are provided showing the advantages of this improved oven calciner compared to current calcining processes.

Work was carried out to determine the quality of catalysts produced from a current commercial-scale moving bed calciner compared to catalysts produced from an improved commercial-scale oven calciner.

The catalyst components were dissolved in water and this formulation was impregnated (coated) on the substrate (FIG. 1, 101). The un-coated substrate had an average length to width (aspect ratio) of 2.94/1.00. The water was removed from the coated substrate in a drying oven (FIG. 1, 102). The coated substrate was then calcined in about 500 kg batches using the improved oven calciners 103 and the commercial-scale moving bed calciner. This material is referred to as the $1^{st}$ pass catalyst. The $1^{st}$ pass catalyst was impregnated a second time 106 with the catalyst formulation, dried 102 and calcined. This material is referred to as the $2^{nd}$ pass catalyst which is the finished catalyst 107.

The properties of the catalysts produced from these two manufacturing processes were compared by quantifying their aspect ratios (the average length to width ratios [L/R] of catalyst particles) and the concentrations of a primary (component #1) and secondary constituent (component #2) in the finished catalysts. In addition, optical microscopy was employed to compare the surfaces of the finished catalysts 104.

Table 1 summarizes the average, relative concentrations of components #1 and #2 for the catalyst produced using this improved oven calciner and the moving bed calciner. The concentrations of components #1 and #2 from the improved oven calciner were within quality specifications established by laboratory-scale production studies. The batch-to-batch variation in composition was about 3%

In comparison, the relative concentrations of components #1 and #2 for the catalyst produced using the moving bed calciner were 9% and 21% lower, respectively, compared to that for the improved oven calciner.

Optical microscopic examination of the catalyst surfaces revealed significant abrasion from the moving bed calcining oven, whereas, no abrasion was observed for catalysts produced from this improved oven calciner. Such losses are not only costly but the resulting catalyst is less efficient in producing the desired fuels and chemicals.

Tables 1 and 2 also present aspect ratios (length/diameter—L/D) for catalysts produced from the two types of calciners. The average aspect ratios for the $1^{st}$ and $2^{nd}$ pass catalysts produced by the improved oven calciner were 2.97 and 2.96, respectively, compared to 2.94 for the substrate. This data demonstrates that this improved oven calciner did not damage the catalyst.

In contrast, the average aspect ratios for the $1^{st}$ and $2^{nd}$ pass catalysts produced by the commercial-scale moving bed calciner were 2.37 and 1.73, respectively, compared to 2.94 for the substrate. This data demonstrates that this moving bed calciner did significant damage to the catalyst.

TABLE 1

Chemical and Physical Properties of Catalysts Manufactured by the Improved Oven Calciner

| | Relative Concentrations of Catalyst Components in the Manufactured Catalyst | | Aspect Ratio (L/D) | |
| --- | --- | --- | --- | --- |
| | (compared to batch #1) | | $1^{st}$ Pass | $2^{nd}$ Pass |
| Samples | Component #1 | Component #2 | Calcination | Calcination |
| Substrate | 0 | 0 | 2.94 | 2.94 |
| Batch #1 | 1.00 | 1.00 | 3.01 | 3.05 |
| Batch #2 | 1.00 | 1.05 | 2.95 | 2.95 |
| Batch #3 | 0.96 | 0.95 | 2.97 | 2.92 |
| Batch #4 | 1.03 | 0.97 | 2.93 | 2.91 |
| Average | 1.00 | 1.00 | 2.97 | 2.96 |

TABLE 2

Chemical and Physical Properties of Catalysts Manufactured by Current Commercial-Scale Moving Bed Calciners

| | Relative Concentrations of Catalyst Components in the Finished Catalyst compared to | | Aspect Ratio (L/D) | |
| --- | --- | --- | --- | --- |
| | batch #1 (Table 1) | | $1^{st}$ Pass | $2^{nd}$ Pass |
| Samples | Component #1 | Component #2 | Calcination | Calcination |
| Substrate | 0 | 0 | 2.94 | 2.94 |
| Batch #1 | 0.87 | 0.85 | 2.20 | 1.65 |
| Batch #2 | 0.82 | 0.80 | 2.56 | 1.77 |
| Batch #3 | 0.95 | 0.75 | 2.37 | 1.74 |
| Batch #4 | 0.99 | 0.75 | 2.41 | 1.75 |
| Average | 0.91 | 0.79 | 2.37 | 1.73 |

Table 3 summarizes the average deviations (%) from manufacturing quality specifications for this improved commercial-scale calcination process compared to a traditional commercial-scale moving bed calcination process. The BET surface area ($m^2/g$) and pore volume (cc/g) were within 4.0% and 4.8% of the quality specifications, respectively for the improved calcination process. The pore volume for the traditional moving bed calcination process was within specifications whereas the surface area was 26% lower.

As summarized in Table 3, the CO conversion rates, conversion of $CO_2$ to products, and the selectivities for the production of gas-phase and solid phase side products were all within 5% of specifications. In contrast, the quality specifications for CO and $CO_2$ conversion efficiency were low by 29% for the traditional calcination process.

TABLE 4

Average Deviations (%) from Performance Quality Specifications for Catalysts produced by the Improved Calcination Process compared to a Traditional Moving Bed Calcination Process

| Catalyst Performance Measurement | Improved Calcining Oven Catalyst | Traditional Calcining Oven Catalyst |
| --- | --- | --- |
| B.E.T. Surface Area | +4.0 | −26 |
| Pore Volume | +4.8 | 0.0 |

TABLE 4-continued

Average Deviations (%) from Performance Quality Specifications for Catalysts produced by the Improved Calcination Process compared to a Traditional Moving Bed Calcination Process

| Catalyst Performance Measurement | Improved Calcining Oven Catalyst | Traditional Calcining Oven Catalyst |
|---|---|---|
| CO Conversion Efficiency (%) | +1.3 | −29 |
| $CO_2$ Conversion Efficiency (%) | +4.8 | −29 |
| Gas-Phase Side Product Selectivity (%) | +1.9 | +45 |
| Solid-Phase Side Product Selectivity (%) | 0.0 | +278 |

REFERENCES

U.S. Patent Application Publications

| 0,288,638 A1 | December 2006 | Schwab |
| 0,132,641 A1 | June 2005 | McCallum et al |

U.S. Patent Documents

| 4,918,041 A1 | April 1990 | Hollstein et al |
| 5,194,068 A1 | March 1993 | Mohr et al |
| 5,874,381 A1 | February 1999 | Bonne et al |
| 6,793,695 B1 | September 2004 | Wilkes et al |
| 7,718,832 B1 | May 2010 | Schuetzle et al |
| 8,394,862 B1 | March 2013 | Schuetzle et al |
| 8,741,001 B1 | June 2014 | Schuetzle et al |
| 9,476,002 B1 | October 2016 | Schuetzle et al |
| 9,631,147 B1 | April 2017 | Schuetzle et al |

OTHER PUBLICATIONS

De Jong, K.: Synthesis of solid catalysts. Wiley-VCH, Verlag GmbH, Weinheim, Germany, pp. 1-422 (2009)

Fischer, N., Claeys, M., Van Steen, E., Niemantsverdriet, H., Vosloo, M.: Syngas convention—fuels and chemicals from synthesis gas: state of the art 2, 275, 1-200 (2016).

Gardezi, S. A., Wolan, J. T., Joseph, B.: Effect of catalyst preparation conditions on the performance of eggshell cobalt/$SiO_2$ catalysts for Fischer-Tropsch synthesis. Applied Catalysis A, 447, 151-163 (2012).

Glasser, B., Chester, A., Catalyst Manufacturing Science and Engineering Consortium, Rutgers University, New Jersey, USA, www.cbe.rutgers.edu/brochure.pdf (2019). Regalbuto, J.: Catalyst preparation science and engineering, CRC Press, 1-488 (2006). Gulf Coast Environmental Systems, 1689 Hawthorne Drive, Conroe, TX 77301; www.service@GCEsystem.com (2018).

Haber, J., Block, J. H., Delmon, B.: IUPAC recommendations on calcination, Pure & Appl. Chem. 67, page 1257 (1995).

Hudlicky, M.: Reductions in organic chemistry, American Chemical Society, Washington D.C., p. 429 (1996)

James, O. O., Maity, S.: Temperature programme reduction (TPR) studies of cobalt phases in gamma-alumina supported cobalt catalysts, Journal of Petroleum Technology and Alternative Fuels, 7, 1-12 (2016).

Jentoft, F. C.: Thermal treatment of catalysts in modern methods in heterogeneous catalysis research; www.fhi-berlin.mpg.de/acnew/department/jentoft_calcination (2003).

Khodakov, A. Y., Chu, W., Fongarland, P.: Advances in the development of novel catalysts for synthesis of long-chain hydrocarbons and clean fuels, Chem. Rev., 107, 1692-1744 (2007).

Munnik, P., deJongh, P. E., deJong, K. P.: Recent developments in the synthesis of supported catalysts, Chem. Rev., 115, 14, 6687-6718 (2015).

Van de Loosdrecht, J., Barradas, S., Visagie, J.: Calcination of Co-based Fischer-Tropsch synthesis catalysts, Topics in Catalysis 26, 121-127(2003).

Vedrine, J. C.: Metal oxides in heterogeneous catalysis—catalysis calcination furnaces, Elsevier, 420-434 (2018).

Zhou, W., Cheng, K., Kang, J., Zhou, C., Subramanian, V., Zhang, Q., Wang, Y.: New horizon in $C_1$ chemistry: breaking the selectivity limitation in transformation of syngas and hydrogenation of $CO_2$ into hydrocarbon chemicals and fuels, Chem. Soc. Rev., 48, 3193-3228 (2019). DOI: 10.1039/C8CS00502H

The invention claimed is:

1. A catalyst production process for $CO_2$ hydrogenation catalysts, wherein catalyst materials are heated homogeneously in a calcining oven and in which the oven heating and gas flow rates are controlled, resulting in the production of catalysts that meet batch-to-batch chemical, physical and performance specifications with a high level of reproducibility, wherein the process comprises the steps of:
   a. loading catalyst materials into a calcining oven, wherein the catalyst materials comprise a metal selected from Ni, Cu, Zn, Mg, Mo or Fe on a support, and wherein the weight percent of metal to support ranges from 0.01% to 20%;
   b. wherein the calcining oven is connected to one or more separate reheating chambers, in which the calcining gas is heated using a thermostatically controlled heat source;
   c. circulating the heated calcining gas from the reheating chambers into the calcining oven in which the gas is distributed over catalyst materials;
   d. recirculating the calcining gas back into the reheating chambers at least 10 times;
   e. increasing the oven temperature in increments ranging from about 0.5° F./min. to about 10° F./min such that the temperature in any area of the oven does not vary more than about 25%;
   f. maintaining the oven at a final calcining temperature for a period of time;
   g. cooling the oven to ambient temperature at a controlled rate ranging from about 2° F./min to about 20° F./min.

2. The catalyst production process of claim 1, wherein the calcining oven is a fixed oven.

3. The catalyst production process of claim 2, wherein the catalyst is contained in solid metal trays.

4. The catalyst production process of claim 2, wherein the catalyst is contained in mesh metal trays.

5. The catalyst production process according to claim 1, wherein the catalyst is evenly filled in one or more oven trays to a depth of from about 2 cm to about 5 cm.

6. A catalyst production process for methanol homologation catalysts, wherein catalyst materials are heated homogeneously in a calcining oven and in which the oven heating and gas flow rates are controlled, resulting in the production of catalysts that meet batch-to-batch chemical, physical and performance specifications with a high level of reproducibility, wherein the process comprises the steps of:
   a. loading catalyst materials into a calcining oven, wherein the catalyst materials comprise a metal selected from Fe, Co, Ni, Rh, Ru, Os, Pt, or Pd on a support, and wherein the weight percent of metal to support ranges from 0.001% to 0.5%;

b. wherein the calcining oven is connected to one or more separate reheating chambers, in which the calcining gas is heated using a thermostatically controlled heat source;

c. circulating the heated calcining gas from the reheating chambers into the calcining oven in which the gas is distributed over catalyst materials;

d. recirculating the calcining gas back into the reheating chambers at least 10 times;

e. increasing the oven temperature in increments ranging from about 0.5° F./min to about 10° F./min such that the temperature in any area of the oven does not vary more than about 25%;

f. maintaining the oven at a final calcining temperature for a period of time;

g. cooling the oven to ambient temperature at a controlled rate ranging from about 2° F./min to about 20° F./min.

7. The catalyst production process of claim 6, wherein the calcining oven is a fixed oven.

8. The catalyst production process of claim 7, wherein the catalyst is contained in solid metal trays.

9. The catalyst production process of claim 7, wherein the catalyst is contained in mesh metal trays.

10. The catalyst production process according to claim 6, wherein the catalyst is evenly filled in one or more oven trays to a depth from about 2 cm to about 5 cm.

11. A catalyst production process for the hydrogenation of carbon compounds, wherein catalyst materials are heated homogeneously in a calcining oven and in which the oven heating and gas flow rates are controlled, resulting in the production of catalysts that meet batch-to-batch chemical, physical and performance specifications with a high level of reproducibility, wherein the process comprises the steps of:

a. loading catalyst materials into a calcining oven, wherein the catalyst materials comprise a metal selected from Ni, Pt, or Pd;

b. wherein the calcining oven is connected to one or more separate reheating chambers, in which the calcining gas is heated using a thermostatically controlled heat source;

c. circulating the heated calcining gas from the reheating chambers into the calcining oven in which the gas is distributed over catalyst materials;

d. recirculating the calcining gas back into the reheating chambers at least 10 times;

e. increasing the oven temperature in increments ranging from about 0.5° F./min to about 10° F./min such that the temperature in any area of the oven does not vary more than about 25%;

f. maintaining the oven at a final calcining temperature for a period of time;

g. cooling the oven to ambient temperature at a controlled rate ranging from about 2° F./min to about 20° F./min.

12. The catalyst production process of claim 11, wherein the calcining oven is a fixed oven.

13. The catalyst production process of claim 12, wherein the catalyst is contained in solid metal trays.

14. The catalyst production process of claim 12, wherein the catalyst is contained in mesh metal trays.

15. The catalyst production process according to claim 11, wherein the catalyst is evenly filled in one or more oven trays to a depth from about 2 cm to about 5 cm.

* * * * *